United States Patent [19]
Colleran et al.

[11] Patent Number: 6,080,195
[45] Date of Patent: Jun. 27, 2000

[54] ROTATABLE AND TRANSLATABLE JOINT PROSTHESIS WITH POSTERIOR STABILIZATION

[75] Inventors: Dennis P. Colleran, Plainville; Justin Dye, Mansfield, both of Mass.

[73] Assignee: Johnson & Johnson Professional, Inc., Raynham, Mass.

[21] Appl. No.: 09/112,252

[22] Filed: Jul. 8, 1998

[51] Int. Cl.[7] .................................................. A61F 2/38
[52] U.S. Cl. .......................................................... 623/20
[58] Field of Search ................................. 623/20, 18, 16

[56] References Cited

U.S. PATENT DOCUMENTS

| | | | |
|---|---|---|---|
| 5,147,405 | 9/1992 | Van Zile et al. | 623/20 |
| 5,387,240 | 2/1995 | Pottenger et al. | 623/20 |
| 5,639,279 | 6/1997 | Burkinshaw et al. | 623/20 |
| 5,683,468 | 11/1997 | Pappas | 623/20 |
| 5,824,096 | 10/1998 | Pappas et al. | 623/20 |
| 5,824,102 | 10/1998 | Buscayret | 623/20 |
| 5,879,392 | 3/1999 | McMinn | 623/20 |
| 5,879,394 | 3/1999 | Ashby et al. | 623/20 |
| 5,906,643 | 5/1999 | Walker | 623/20 |

FOREIGN PATENT DOCUMENTS

| | | | |
|---|---|---|---|
| 592750 | 4/1994 | European Pat. Off. | 623/20 |
| 3529894 | 3/1987 | Germany | 623/20 |

*Primary Examiner*—Michael J. Milano
*Assistant Examiner*—Alvin Stewart
*Attorney, Agent, or Firm*—Nutter, McClennen & Fish, LLP

[57] ABSTRACT

A joint prosthesis system includes a tibial bearing insert, a tibial tray, a separate stabilizing post and a femoral component that are joinable to each other. The tibial bearing insert is mounted so that it can both rotate and translate with respect to the tibial tray. The stabilizing post and the femoral component cooperate to force roll back of the femoral component with respect to the tibial components.

20 Claims, 10 Drawing Sheets

ROTATABLE AND TRANSLATABLE JOINT PROSTHESIS WITH POSTERIOR STABILIZATION

CROSS REFERENCE TO RELATED APPLICATIONS

Not applicable.

STATEMENT REGARDING FEDERALLY SPONSORED RESEARCH

Not applicable.

BACKGROUND OF THE INVENTION

The invention relates to joint prostheses. More particularly, the invention is directed to components of knee joint prostheses that have a tibial bearing insert which can rotate and translate with respect to the tibial tray upon which it is mounted.

Joint replacement surgery is quite common and enables many individuals to function normally when otherwise it would not be possible to do so. Artificial joints are normally composed of metallic, ceramic and/or plastic components that are fixed to existing bone.

Knee arthoplasty is a well known surgical procedure by which a diseased and/or damaged natural knee joint is replaced with a prosthetic knee joint. Typical knee protheses include a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

Typically, the tibial tray is mounted within the tibia of a patient. The tibial bearing insert, which is usually made of ultra high molecular weight polyethylene (UHMWPE) is mounted upon the superior surface of the tibial tray. Load and stress are placed upon the knee prosthesis, and particularly on the tibial bearing insert, during normal daily use. These forces may lead to the displacement or dislocation of the insert from the tibial tray. To accommodate these forces, and to reduce the chances for dislocation, some tibial components of knee prostheses have been designed to allow rotation of the tibial bearing insert relative to the proximal or superior surface of the tibial tray, about the longitudinal axis of the prosthesis. Such rotation, when controlled, can increase the contact area between the femoral condyles and the tibial bearing insert throughout the range of knee motion, thus reducing stress on the tibial bearing insert.

Some knee prostheses that allow for rotation of the tibial bearing insert also permit translation, or roll back, of the tibial bearing insert in the anterior-posterior direction.

There is often a trade-off between the longevity of a knee prosthesis and the overall performance or kinematics of the prosthesis. It has been difficult to optimize both longevity and kinematics. Rotatable knee prostheses have provided some benefits. However, some rotatable knee prostheses that permit translation of the tibial bearing insert in the medial-lateral and anterior-posterior directions can yield some degree of anterior-posterior instability. This problem is overcome, in some instances, by posterior stabilized prostheses. However, in such designs, movement of the tibial bearing insert in the anterior-posterior direction, or roll back, can place undesirable levels of stress on the stabilizing post of the prosthesis.

Despite the benefits of existing designs for knee joint prostheses having a rotatable tibial component, there remains a need for prostheses that still reduce stress, provide optimal roll back and maintain optimal contact of the tibial and femoral components to accommodate the stresses placed upon the knee.

SUMMARY OF THE INVENTION

The invention is directed to a joint prosthesis system which includes first and second tibial components, a separate stabilizing post and a femoral component. The second tibial component can rotate and translate with respect to the first tibial component. The stabilizing post and the femoral component cooperate to force rollback of the femoral component while the system maintains a close match between the femoral and tibial condyles.

A first tibial component has a superior mounting surface and an inferior bone contacting surface. The superior mounting surface of the first tibial component includes a cavity defined by inner side and distal walls. The second tibial component has an inferior surface that mounts upon the superior surface of the first tibial component, a superior articulation surface, and an opening extending between the inferior and superior surfaces. The second tibial component is rotatably and translatably mountable upon the superior mounting surface of the first tibial component. Further, the stabilizing post, which has proximal and distal ends, is adapted to be inserted through the opening of the second tibial component and is matable within the cavity of the first tibial component. The post includes a proximal head portion having surfaces which engage a portion of the femoral component.

The femoral component of the system has a first surface mountable on a distal end of a femur of a patient and a second articulation surface that includes two adjacent condyles that are joined by an intermediate surface. The intermediate surface includes first and second engaging surfaces adapted for engagement with superior and posterior engaging surfaces of the stabilizing post.

The system may also include a ring member adapted to fit within the opening of the second tibial component as an articulation surface between the second tibial component and the stabilizing post.

DETAILED DESCRIPTION OF THE INVENTION

The invention provides a construction for a knee joint prosthesis system 10 which allows rotation and translation of the tibial component while providing for enhanced posterior stability. The design of the prosthesis system of the invention combines enhanced longevity with improved kinematics.

Figure 1:
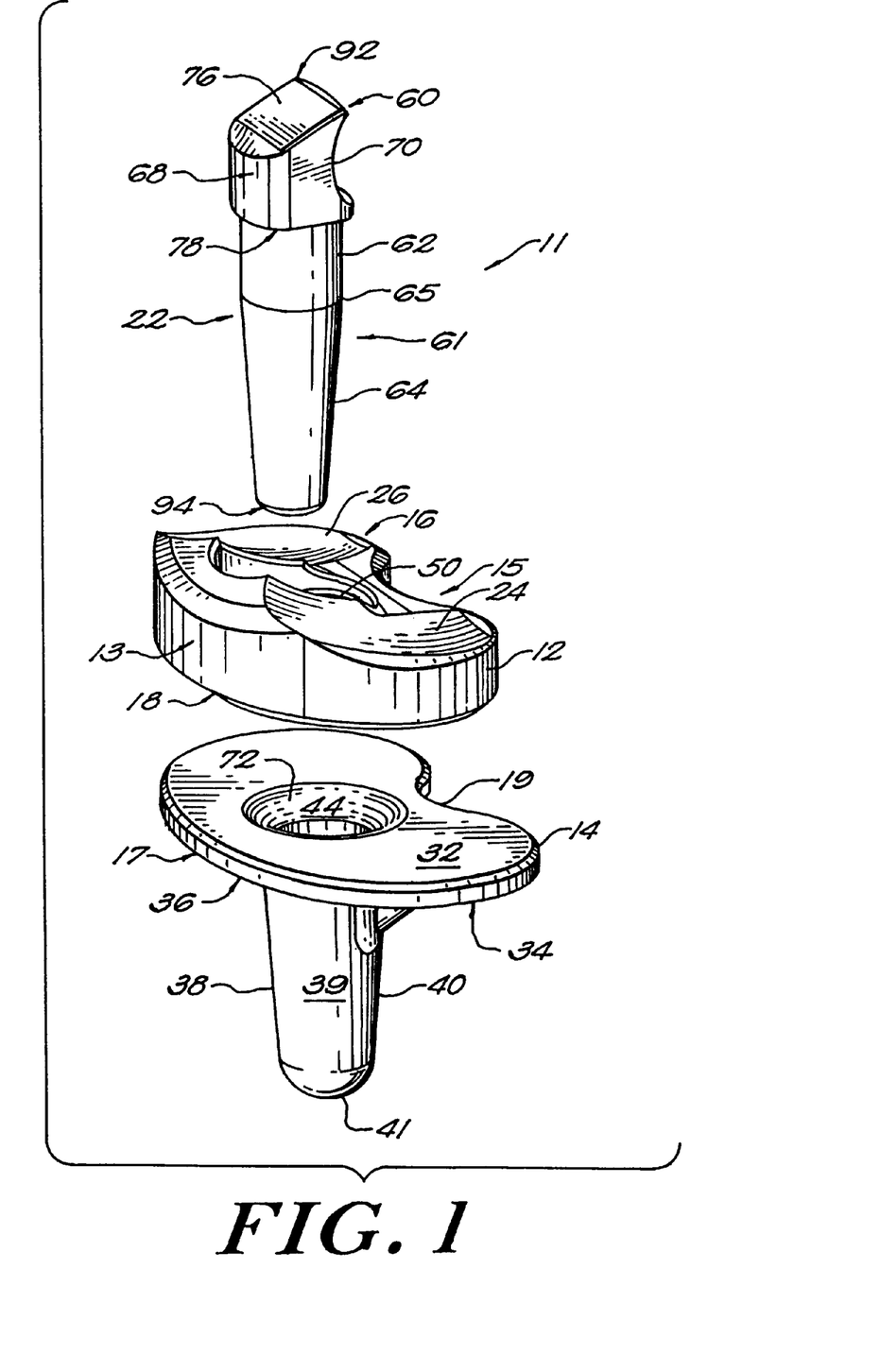
FIG. 1 is an exploded perspective view of the tibial portion of a knee joint prosthesis system according to the present invention.
Figure 2:
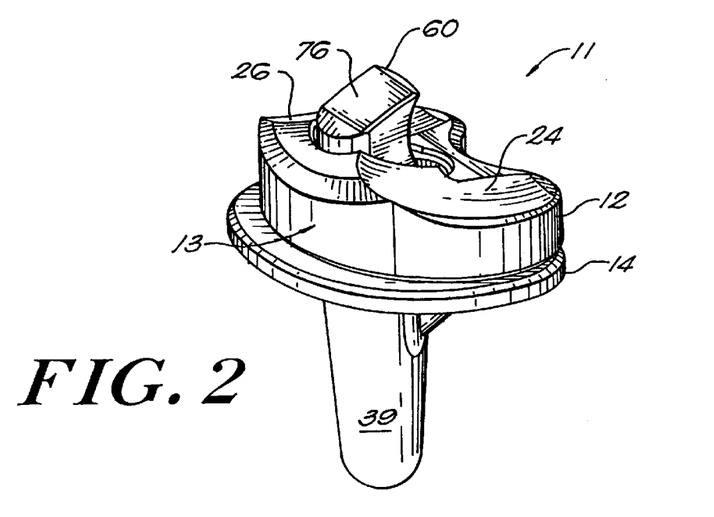
FIG. 2 is a perspective view of the assembled components shown in FIG. 1.
Figure 3:
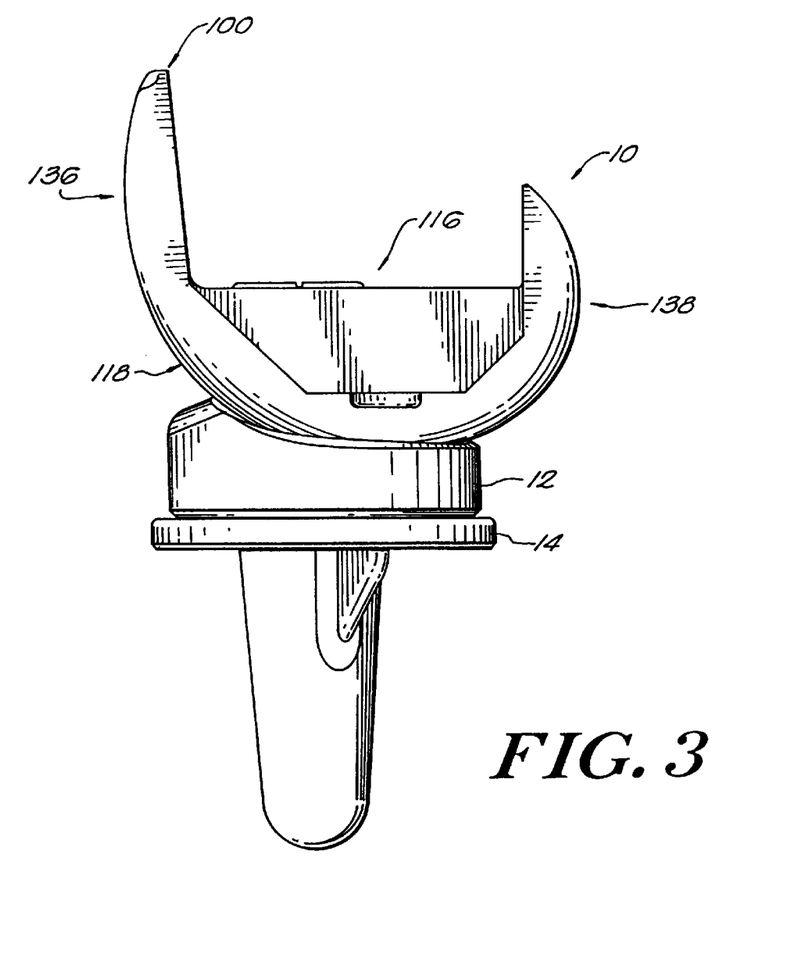
FIG. 3 is a side view of a knee joint prosthesis system according to the present invention at about 0° flexion.
Figure 4:
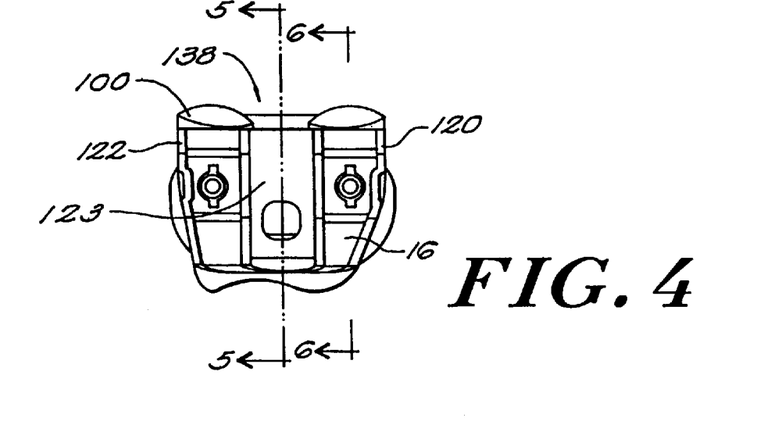
FIG. 4 is a top view of the prosthesis system shown in FIG. 3.

Referring to FIGS. 1 and 2, a tibial component 11 of the joint prosthesis system 10 includes a first component in the form of a tibial tray 14, a second component in the form of a tibial bearing insert 12 and a third component in the form of a separate stabilizing post 22. The mounting of the tibial bearing insert 12 to the tibial tray 14 is such that the tibial bearing insert 12 is able to rotate and translate with respect to a proximal or superior surface 32 of the tibial tray 14. The system 10 further includes a fourth component in the form of a femoral component 100 which is illustrated in FIGS. 3–10.

The tibial bearing insert 12 has an anterior side 13, a posterior side 15, a superior articulation surface 16 and an inferior mating surface 18. The superior surface 16 may have one or more condylar elements that are adapted to articulate with complementary condyle(s) of a femoral component as shown in FIGS. 3–10. Specifically, the condylar elements include lateral and medial condyles 24, 26. The tibial bearing insert 12 further has an opening 50 extending therethrough from the superior articulation surface 16 to the inferior mating surface 18. The opening 50 may be of any suitable shape which allows for translation and rotation of the tibial bearing insert 12. In one embodiment, discussed below with respect to FIG. 11, the opening 50 is elongated in the anterior-posterior direction.

Figure 5A:
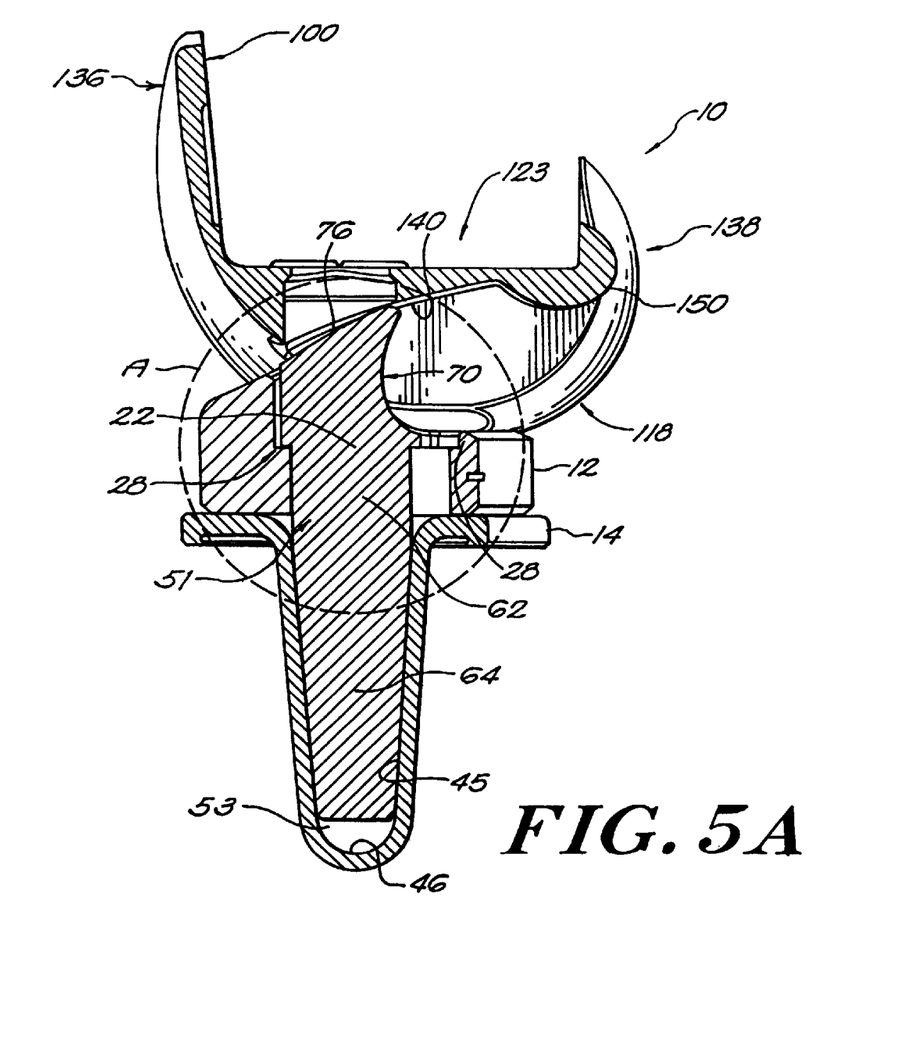
FIG. 5A is a side sectional view of the assembled components of the prosthesis system shown in FIG. 4, at line 5—5.
Figure 5B:
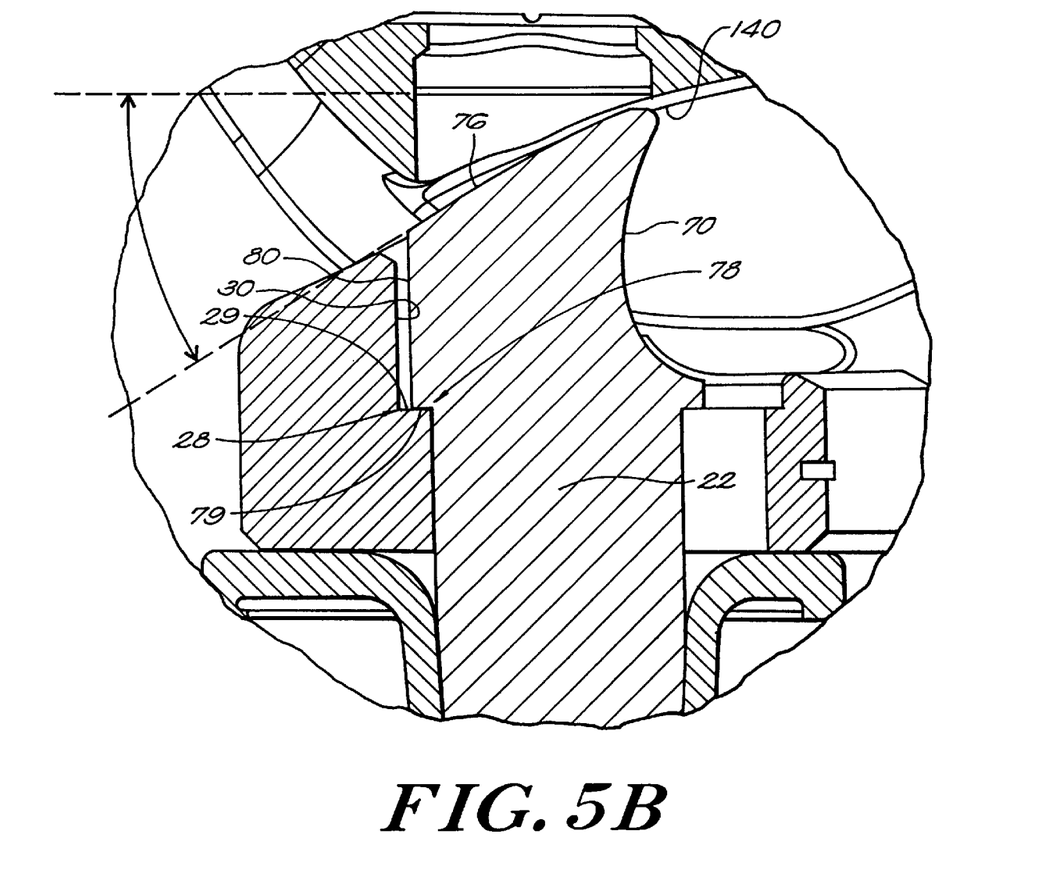
FIG. 5B is a detail view of a portion "A" of FIG. 5A.
Figures 6, 7:
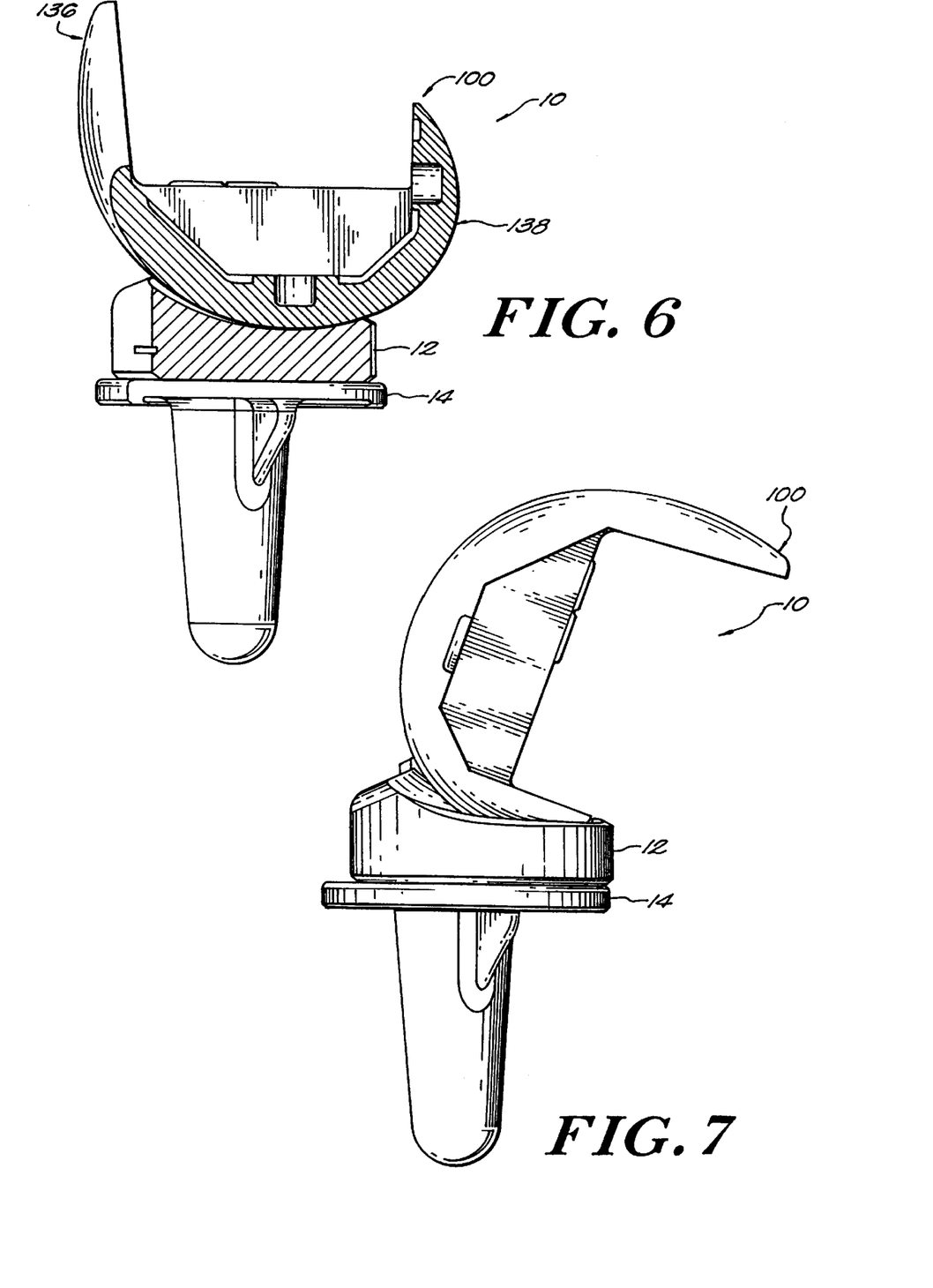
FIG. 6 is a side sectional view of the prosthesis system of FIG. 4, at line 6—6.
FIG. 7 is a side view of the prosthesis system according to the present invention at about 90° flexion.
Figure 8:
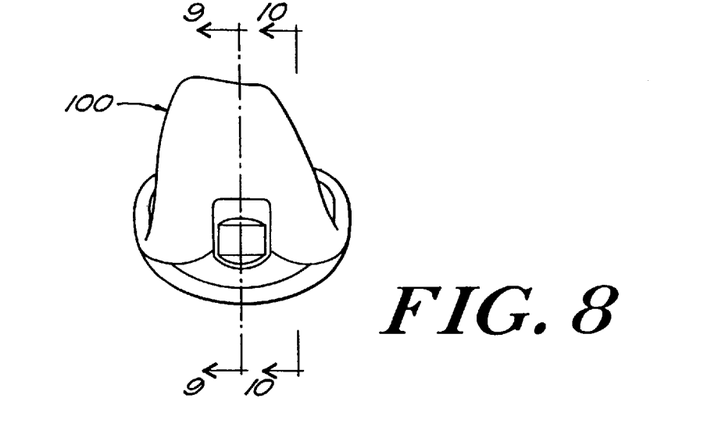
FIG. 8 is a top view of the prosthesis system shown in FIG. 7.

In an exemplary embodiment, shown in FIGS. 5A and 5B, at least one mating shoulder 28 is formed within opening 50. The mating shoulder 28 extends in an arc about the inner circumference of the opening 50. The shoulder 28 may be in the form of a continuous arc, or it may be formed in two or more arcs. As illustrated, the shoulder 28 includes a proximally facing surface 29. The surface 29 may form virtually any angle between 45° and 90° with the inner walls 30 of opening 50. Preferably, however, the surface 29 extends from inner wall 30 at an angle of 90°.

The inner walls 30 of the opening 50 define a first opening area proximal of the proximally facing surface 29 and a second smaller opening area distal of the surface 29. The first opening has a dimension (w) in the medial-lateral direction in the range of about 0.5 to 0.8 inches and preferably 0.65 inches, and a dimension (1) in the anterior-posterior direction in the range of about 0.8 to 1.0 inches and preferably 0.925 inches. The second smaller opening has a dimension (w') in the medial-lateral direction in the range of about 0.5 to 0.7 inches and preferably 0.6 inches, and a dimension (1') in the anterior posterior direction in the range of about 0.7 to 0.9 inches and preferably 0.8 inches.

As further illustrated in FIGS. 5A and 5B, the shoulder 28 cooperates to seat a complementary distal facing shoulder 78 formed on stabilizing post 22. The engagement of shoulders 28 and 78 ensure the proper positioning of post 22 within the tibial tray 14 and the tibial bearing insert 12.

The tibial tray 14 includes an anterior side 17, a posterior side 19, a superior mating surface 32 and an inferior bone contacting surface 34. The bone contacting surface 34 has a first portion 36 that represents an area of the inferior bone contacting surface 34 that mounts upon the proximal surface of a resected tibia (not shown). A second portion 38 of the bone contacting surface 34 extends from the first portion 36 and is adapted to extend into a cavity (not shown) formed within a patient's tibia. Preferably, the second portion 38 is an elongate tibial stem 39 that extends from the first portion 36. The tibial stem 39 has outer side and distal walls 40, 41. The outer side walls 40 of the tibial stem 39 may be smooth, or they may have irregular surface features (not shown) to enhance bone fixation.

The superior surface 32 of the tibial tray 14 includes an aperture 72 (which may be of any suitable shape, e.g., substantially circular) that communicates with a mating cavity 44. In an illustrated embodiment, shown in FIG. 5A, the mating cavity 44 is a blind cavity, defined by interior side walls 45 that extend into the tibial stem. The mating cavity 44 terminates in an interior distal wall 46 that may be substantially cone-shaped, or formed in another shape that is suitable for receiving the stabilizing post 22.

One of ordinary skill in the art will readily appreciate that the dimensions of the cavity 44 and the stabilizing post 22 may vary. In one embodiment, the cavity 44 has a diameter that tapers from proximal 51 to distal 53 ends thereof at an angle in the range of about 0° to 10°. The diameter at the proximal end 51 is in the range of about 10 to 20 mm and the diameter at the distal end 53 is in the range of about 5 to 20 mm. The cavity 44 preferably has a depth in the range of about 25 to 60 mm and is sized to accept the stabilizing post 22.

The stabilizing post 22 includes a proximal end 92 and a distal end 94. The proximal end 92 of the stabilizing post 22 includes an enlarged head portion 60. The head portion 60 includes an anterior surface 68, a posterior engagement surface 70, and a superior engagement surface 76. The distal portion of head 60 includes mating shoulder 78.

The stem portion 61 of stabilizing post 22 extends distally from the head portion 60. The stem portion 61 includes a proximal stem section 62 and a distal stem section 64. In one embodiment, proximal stem section 62 has a substantially uniform diameter in the range of about 10 to 20 mm. The distal stem section 64 has a diameter that tapers distally, ranging from about 10 to 20 mm adjacent the interface 65 between proximal and distal stem sections to about 5 to 20 mm at the distal end 94 of the stabilizing post 22. The distal stem section 64 tapers from the interface 65 to the distal end 94 at an angle in the range of about 0° to 10°. The dimensions of the stem portion 61 of stabilizing post 22 are such that when engaged within cavity 44 of the tibial tray 14, the stabilizing post 22 cannot be dislodged and is axially stable.

The overall length of the stabilizing post 22, including head portion 60, is in the range of about 40 to 80 mm. The length of the stem portion 61 of post 22, from the mating shoulder 78 to distal end 94, is generally in the range of about 20 to 60 mm.

As shown in FIGS. 5A and 5B, the inferior mating shoulder 78 of the stabilizing post 22 includes a distal facing surface 79 and a vertical surface wall 80. The mating shoulder 78 is formed due to the dimensions of the post 22 in which the proximal stem section 62 has a diameter such that it is undercut with respect to the superior vertical wall 80 of the head portion. The distal facing surface 79 of shoulder 78 may be angled with respect to wall 80 at virtually any angle between 45° and 90°. However, the angle of surface 80 should be complementary with proximally facing surface 29 within opening 50 of tibial bearing insert 12. The dimensions by which surface 79 overhang proximal stem section 62 should be sufficient to ensure and maintain engagement with the proximally facing surface 29 within opening 50 of the tibial bearing insert 12. Preferably, this dimension is about 0.5 to 4.0 mm.

As shown in FIGS. 2–10, the tibial bearing insert 12, the tibial tray 14, and the stabilizing post 22 are adapted to fit together to form a tibial component of a knee joint prosthesis. The stem portion 61 of the stabilizing post 22 is inserted within the opening 50 of the tibial bearing insert 12 such that extends into the mating cavity 44 of the tibial tray 14. Typically, the tapered distal stem section 64 of the stabilizing post 22 resides in the cavity 44 of the tibial tray 14 and the proximal stem section 62 is encompassed within the opening 50 of the tibial bearing insert 12. The engagement of the tibial bearing insert 12, the tibial tray 14 and the stabilizing post 22 is such that the tibial bearing insert 12 remains independent of the tibial tray 14 and the stabilizing post 22 so that it is able to rotate with respect to these components.

Figure 11:
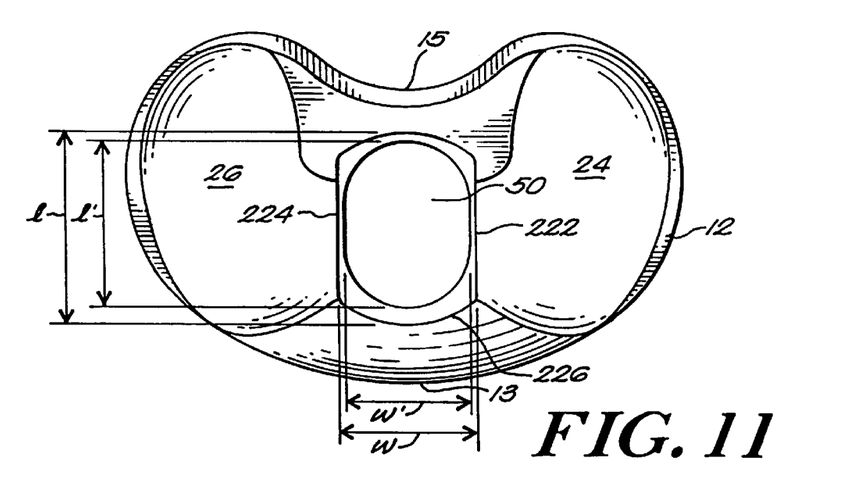
FIG. 11 is a top view of a tibial bearing insert component of the joint prosthesis system according to the present invention.

As shown in FIG. 11, the opening 50 of the tibial bearing insert 12 is elongated in the anterior-posterior direction. the dimensions of this opening can vary depending upon the performance and characteristics desired for a given prosthesis. Generally, however, the opening 50 has an anterior-posterior dimension, measured from anterior end 226 to posterior end 228, of about 2 to 4 mm. These dimensions generally provide about 2 to 6 mm of clearance between a centrally positioned post 22 and anterior and posterior end walls 226, 228. Accordingly, the tibial bearing insert 12 is permitted to move about 2 to 6 mm from a centrally disposed position to its anterior and posterior extremes, with the movement being substantially in the posterior direction.

In one embodiment some clearance is provided between post 22 and the lateral and medial 222, 224 side walls of opening 50. Such a construction permits a small degree of medial-lateral translation of the tibial bearing insert 12 relative to the tibial tray 14. Generally, the amount of clearance between stabilizing post 22 and medial and lateral side walls 222, 224, is about 0.25 mm. Hence, the tibial bearing insert 12 is permitted to translate up to about 0.25 mm in the medial and lateral directions relative to the tibial tray 14.

As shown in FIG. 2, the proximal end 92 of the stabilizing post 22 protrudes above the superior articulation surface 16 of the tibial bearing insert 12 when the tibial component of the prosthesis system is assembled. The stabilizing post 22 may also rotate with respect to the tibial tray 14. This configuration permits the stabilizing post 22 to engage the femoral component 100 in the manner described below.

Referring to FIGS. 3–10, the femoral component 100 has an anterior side 136 and a posterior side 138, and it includes a first surface 116 which is mountable upon the distal end of a patient's femur and a second articulation surface 118. The articulation surface 118 includes adjacent lateral 120 and medial 122 condyles which are joined to one another by an intermediate or intercondylar region 123. As shown in FIGS. 2–10, the lateral and medial condyles 120, 122 of the femoral component 100 abut and are able to articulate with the lateral and medial condyles 24, 26 of tibial bearing insert 12. The condyles 120, 122 of femoral component 100 and the condyles 24, 26 of tibial bearing insert 12 are configured such that a relatively large contact area is achieved when the condyles of the femoral component and the condyles of the tibial bearing insert mount upon each other. In an exemplary embodiment, each condyle 120, 122 is generally ellipsoid in shape and is of a curved, convex shape in both the anterior-posterior direction and in the medial-lateral direction.

Figure 9:
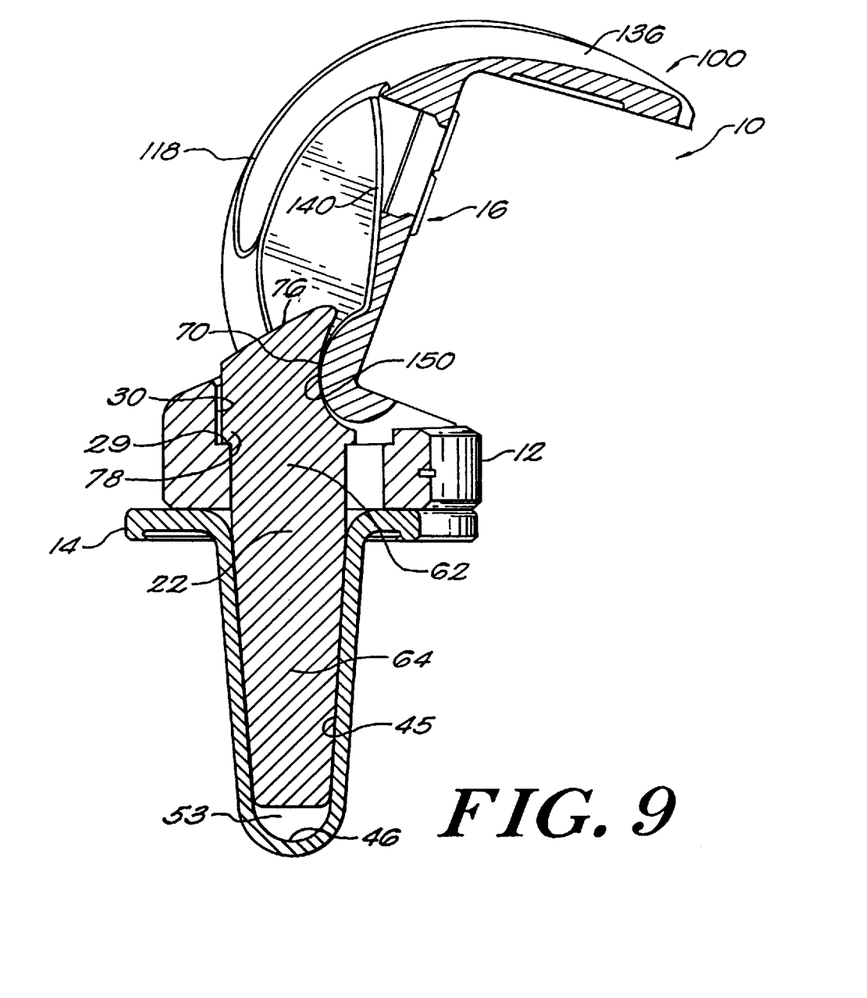
FIG. 9 is a side sectional view of the prosthesis system of FIG. 8, at line 9—9.
Figure 10:
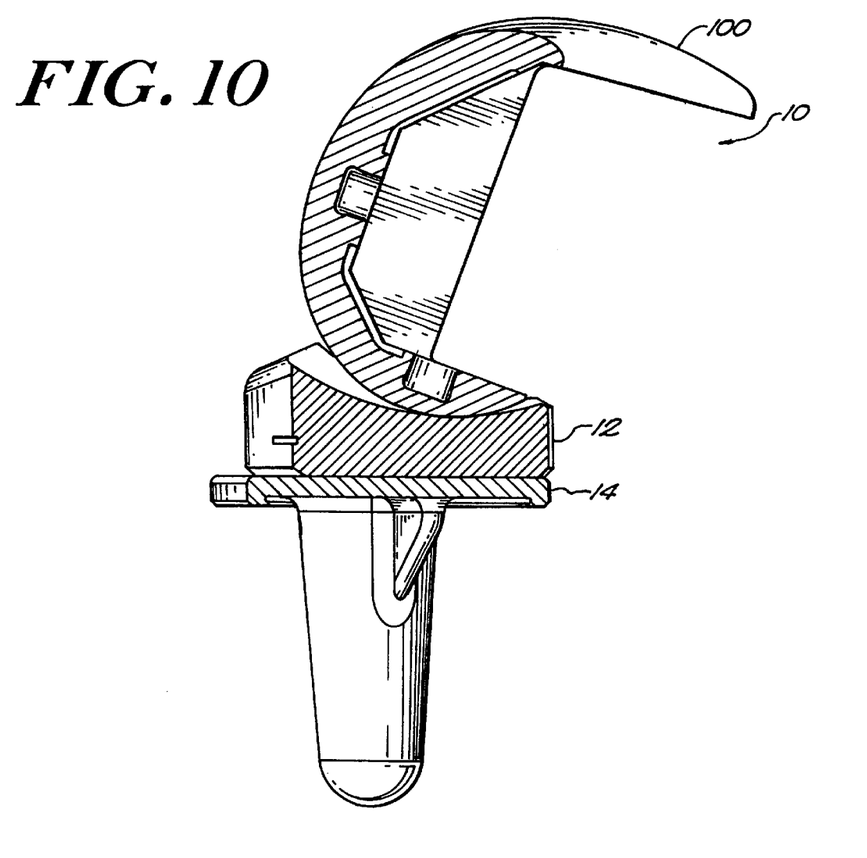
FIG. 10 is a side sectional view of the prosthesis system of FIG. 8, at line 10—10.

As shown in FIGS. 5A and 9, the intercondylar region 123 includes a first engaging surface 140 and a second engaging surface 150. The first engaging surface 140 is oriented at an angle complementary to that of the superior engaging surface 76 of the stabilizing post 22. Surface 140 extends from the anterior side 136 of the femoral component 100 towards the posterior side 138 of the femoral component 100. The posterior portion of surface 140 meets the second engaging surface 150 located proximate the posterior side 138 of the femoral component 100. The second engaging surface 150 has a curved cam-like shape that is generally complementary to the curved posterior engagement surface 70 of the stabilizing post 22.

The movement of the second engaging surface 150 of the femoral component 100 relative to the curved posterior engagement surface 70 of the stabilizing post 22 produces a posterior translation of the femoral component 100 resulting from the flexion (rotation) of the femoral component 100. The shape of the second engaging surface 150 is dependent on factors such as the femoral anterior-posterior profile, the insert topography and the shape/form of the curved posterior engagement surface 70. While the posterior engagement surface 70 is defined by a curvature having a single radius, the second engaging surface 150 may be constructed with two or more radii. By changing the shape of the second engaging surface 150, the motion of the femur during flexion and the kinematics of the knee can be modified.

As shown in FIGS. 3–6, when the prosthesis system is at about 0° of flexion, the first engaging surface 140 of the femoral component 100, abuts or contacts the superior engaging surface 76 of the stabilizing post 22. In this position, the tibial bearing insert 12 is at a first, generally centered position relative to the tibial tray 14.

As shown in FIGS. 7–10, when the prosthesis system is at about 90° of flexion, the second engaging surface 150 of the femoral component 100 abuts or contacts the posterior engagement surface 76 of the stabilizing post 22. In this position, the tibial bearing insert is at a second position relative to the tibial tray 14. As is evident from an examination of, for example, FIGS. 6 and 10, the tibial bearing insert 12 has moved posteriorly during the transition from 0° flexion to 90° flexion. Consequently, optimal roll back of the femoral component with respect to the tibial component is achieved, thereby placing the tibia of a patient anteriorly during flexion of the knee. Consequently, quadriceps muscle efficiency is improved for the patient as a result of the placement of the femur in this position.

Another embodiment of the knee joint prosthesis system is shown in FIGS. 12–16. In this embodiment, the prosthesis system includes a tibial bearing insert 12, a tibial tray 14, a sleeve or ring member 20 and a separate stabilizing post 22. The ring member 20 is adapted to mate with the tibial bearing insert 12 and act as an articulation surface between the tibial bearing insert 12 and the stabilizing post 22 as the tibial bearing insert 12 translates and rotates.

Figure 12:
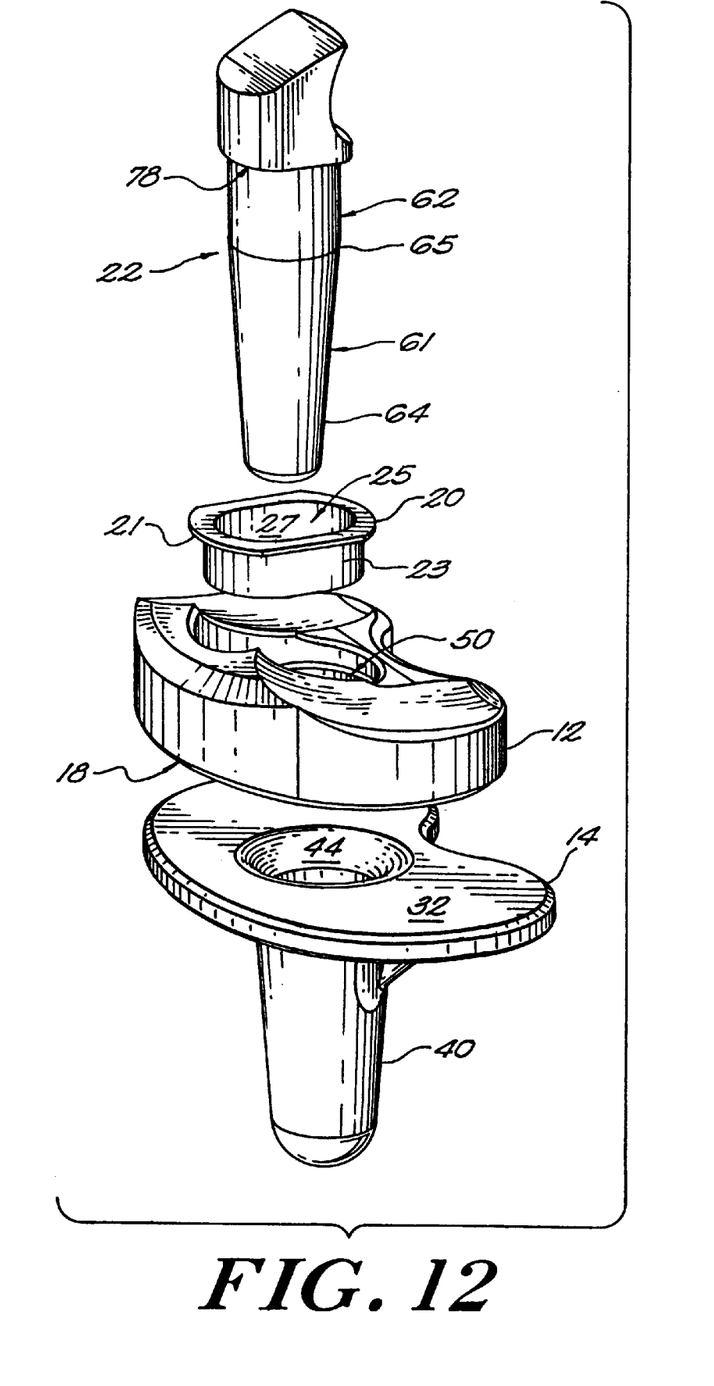
FIG. 12 is an exploded perspective view of another embodiment of the knee joint prosthesis.
Figure 13:
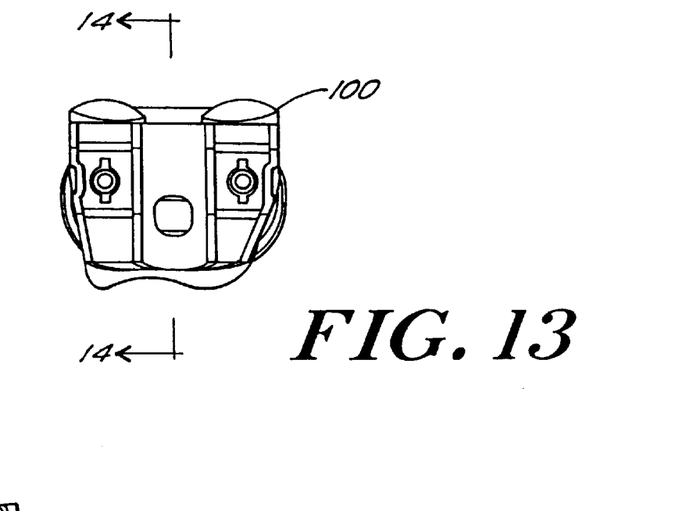
FIG. 13 is a top view of the knee joint prosthesis shown in FIG. 12, at about 0° flexion.

The ring member 20 includes a flange portion 21 which may extend partially or entirely around the circumference of ring member 20. The flange portion 21 defines an opening 25 which is elongated in the anterior-posterior direction in similar fashion to opening 50 of the tibial bearing insert 12. A sidewall portion 23 extends distally from the flange portion 21 and is dimensioned to extend from the proximally facing surface 29 to the inferior mating surface 18 of the tibial bearing insert 12 when the components are assembled.

The ring member 20 can be made from a variety of materials known to those having ordinary skill in the art. Suitable materials are compatible with stabilizing post 22, possess good wear resistance as well as low friction. Exemplary materials include titanium, titanium alloys, cobalt-chromium alloys, and ultrahigh molecular weight polyethylene.

One of ordinary skill in the art will likewise appreciated that the stabilizing post 22 can also be made of a variety of suitable materials, including those from which the ring member 20 may be made.

Figure 14:
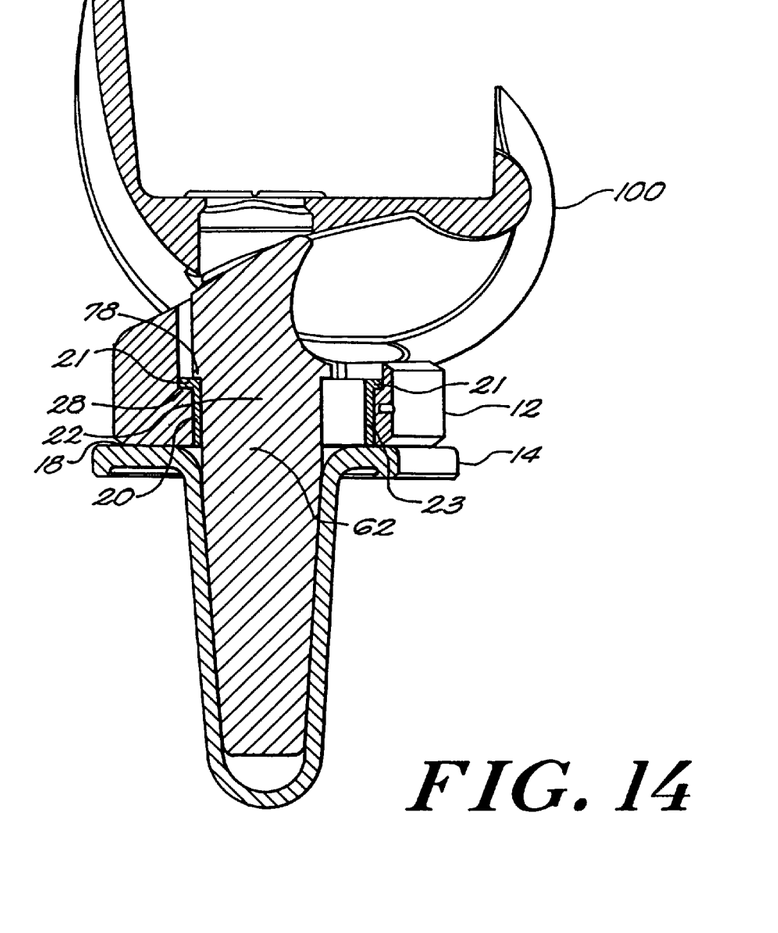
FIG. 14 is a side sectional view of the assembled components of the prosthesis system shown in FIG. 13, at line 14—14.
Figure 15:
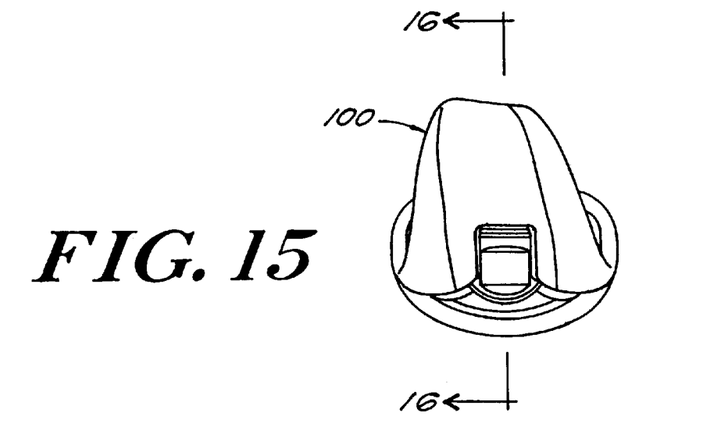
FIG. 15 is a top view of the embodiment of FIG. 12 at about 90° flexion.
Figure 16:
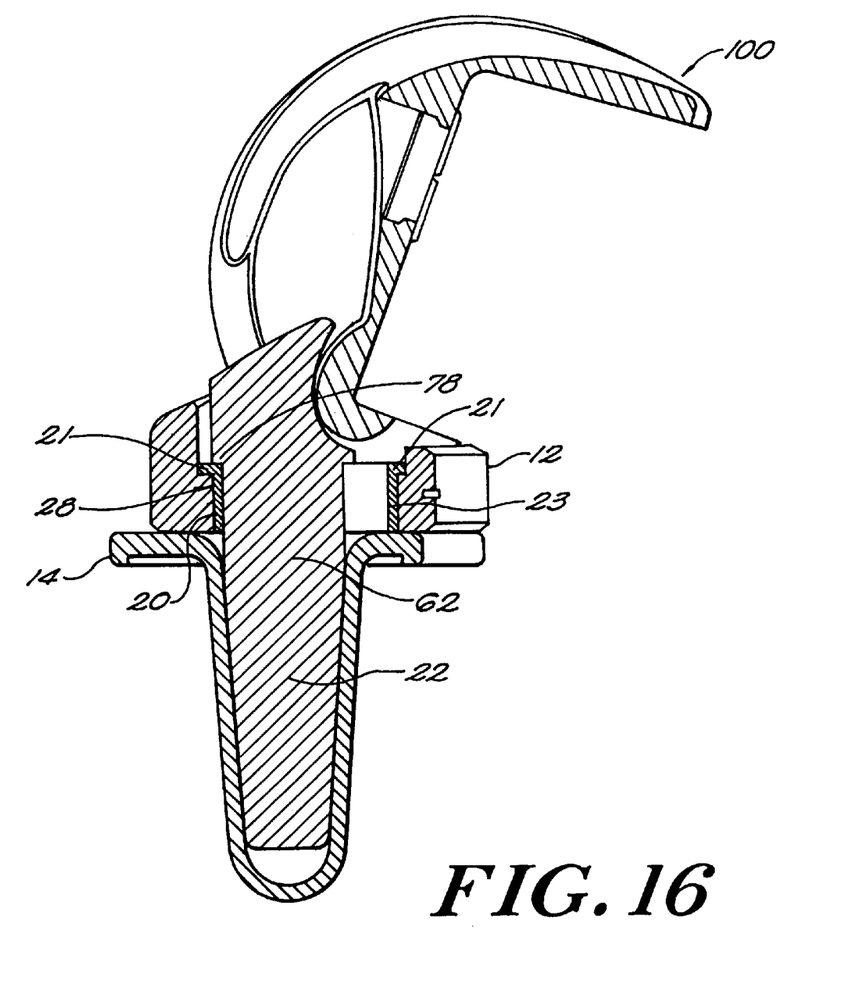
FIG. 16 is a side sectional view of the prosthesis system of FIG. 15, at line 16—16.

As shown in FIGS. 14 and 16, the ring member 20 is seated within opening 50 of the tibial bearing insert 12. In this arrangement, the flange portion 21 of ring member 20 abuts mating shoulder 28 to secure ring member 20 in place with respect to the tibial bearing insert 12. Typically, when the system is assembled, the proximal stem section 62 of the stabilizing post 22 is encompassed within a circumferential inner sidewall 27 of ring member 20. In this configuration, the distal facing shoulder 78 formed on stabilizing post 22 is seated on the flange portion 21 of ring member 20.

One of ordinary skill in the art will further appreciate that minor modifications may be made to the invention described herein without departing from its intended scope. All references noted herein are expressly incorporated by reference in their entirety.

What is claimed is:

1. A non-hinged hinge joint prosthesis system, comprising:
   a first component having a superior mounting surface and an inferior bone contacting surface, the superior mounting surface having a cavity defined by inner side and distal walls;
   a second component having an opening extending therethrough, from a superior articulation surface to an inferior mating surface, the inferior mating surface of the second component being rotatably mountable upon the superior mounting surface of the first component; and
   a separate stabilizing post having proximal and distal ends, the proximal end including a head portion having a superior engaging surface, an inferior mating shoulder, an anterior surface, and a posterior engaging surface, the post being insertable through the opening of the second component and matable within the cavity of the first component such that the stabilizing post, the first component, and the second component are secured to one another and such that the proximal end of the stabilizing post protrudes above the superior articulation surface of the second component.

2. The system of claim 1, wherein the inferior mating shoulder engages a complementary mating shoulder formed in the opening of the second component.

3. The system of claim 1, further comprising:
   a femoral component having a first surface mountable on a distal end of a femur of a patient and a second articulation surface including two adjacent, semi-parallel condyles joined by an intermediate surface, the intermediate surface including a first engaging portion and a second engaging portion.

4. The system of claim 3, wherein the first engaging portion engages the superior engaging surface of the stabilizing post when the system is at about 0° hyperextension and the second engaging portion engages the posterior engaging surface of the stabilizing post when the system is at about 70°–90° flexion.

5. The system of claim 3, wherein each condyle is of a curved, convex shape in both an anterior-posterior direction and a medial-lateral direction.

6. The system of claim 1, wherein the cavity of the first component tapers from a first diameter at a proximal end to a second diameter at a distal end.

7. The system of claim 6, wherein the cavity has a diameter that tapers from proximal to distal ends thereof at an angle in the range of about 0° to 10°.

8. The system of claim 1, wherein the stabilizing post includes an elongate member, disposed distally of the proximal end thereof, having a member mounting surface that is mountable within the cavity of the first component.

9. The system of claim 7, wherein the elongate member has a proximal portion with a first, uniform diameter, and a distal portion with a diameter that tapers distally.

10. The system of claim 1, wherein the opening of the second component is elongated in the anterior-posterior direction.

11. The system of claim 10, wherein the second component is permitted to translate in the anterior-posterior direction up to about 2 to 6 mm with respect to the first component.

12. The system of claim 10, wherein the second component is permitted to translate in the medial-lateral direction up to about 0.25 mm with respect to the first component.

13. The system of claim 10, further comprising a ring member mounted within the opening of the second component.

14. The system of claim 13, wherein the stabilizing post engages a flange portion formed on the ring member.

15. The system of claim 1, wherein the first component is a tibial tray and the second component is a tibial bearing insert.

16. A non-hinged hinge joint prosthesis system, comprising:
   a tibial tray having a superior mounting surface and an inferior bone contacting surface, the superior mounting surface having a cavity defined by inner side and distal walls;
   a tibial bearing component having an anterior-posteriorly elongated opening extending therethrough, from a superior articulation surface to an inferior mating surface, the inferior mating surface of the tibial bearing component being rotatably mountable upon the superior mounting surface of the tibial tray;
   a separate stabilizing post having proximal and distal ends, the post being insertable through the opening of the tibial bearing component and matable within the cavity of the tibial tray such that the tibial bearing component is able to rotate and translate with respect to the stabilizing post and such that the proximal end of the stabilizing post protrudes above the superior articulation surface of the tibial bearing component; and a femoral component having a first surface and an opposed articulation surface, including two adjacent condyles joined by an intermediate surface, the intermediate surface being non-hingedly engageable with a proximal portion of the stabilizing post.

17. The system of claim 16, wherein the tibial bearing component is permitted to translate in the anterior-posterior direction up to about 2 to 6 mm with respect to the tibial tray.

18. The system of claim 16, wherein the tibial bearing component is permitted to translate in the medial-lateral direction up to about 0.25 mm with respect to the tibial tray.

19. The system of claim 16, wherein the tibial bearing component is permitted to rotate about with respect to the tibial tray.

20. The system of claim 16, further comprising a ring member mounted within the elongated opening of the tibial bearing component.

\* \* \* \* \*